(12) United States Patent
Chen et al.

(10) Patent No.: US 7,241,457 B2
(45) Date of Patent: Jul. 10, 2007

(54) OSMOTICALLY DRIVEN ACTIVE AGENT DELIVERY DEVICE PROVIDING AN ASCENDING RELEASE PROFILE

(75) Inventors: Guohua Chen, Sunnyvale, CA (US); Rupal A. Ayer, Cupertino, CA (US); Scott Lautenbach, San Mateo, CA (US)

(73) Assignee: Alza Corporation, Mountain View, CA (US)

( * ) Notice: Subject to any disclaimer, the term of this patent is extended or adjusted under 35 U.S.C. 154(b) by 31 days.

(21) Appl. No.: 10/953,895

(22) Filed: Sep. 29, 2004

(65) Prior Publication Data
US 2005/0107772 A1 May 19, 2005

Related U.S. Application Data

(60) Provisional application No. 60/507,920, filed on Sep. 30, 2003.

(51) Int. Cl.
*A61K 9/22* (2006.01)
(52) U.S. Cl. .................... 424/468; 604/892.1
(58) Field of Classification Search ........ 424/422–428, 424/453, 457, 464, 468, 472; 604/890.1, 604/892.1
See application file for complete search history.

(56) References Cited

U.S. PATENT DOCUMENTS

| | | | |
|---|---|---|---|
| 3,625,214 A * | 12/1971 | Higuchi ...................... | 424/424 |
| 4,874,388 A | 10/1989 | Wong et al. | |
| 4,976,966 A * | 12/1990 | Theeuwes et al. .......... | 424/473 |
| 5,234,693 A | 8/1993 | Magruder et al. | |
| 5,279,608 A | 1/1994 | Cherif Cheikh | |
| 5,336,057 A | 8/1994 | Fukuda et al. | |
| 5,728,396 A | 3/1998 | Peery et al. | |
| 5,836,935 A | 11/1998 | Ashton et al. | |
| 5,976,109 A | 11/1999 | Heruth | |
| 5,985,305 A | 11/1999 | Peery et al. | |

(Continued)

OTHER PUBLICATIONS

Darney, Philip D., "Subdermal progestin implant contraception," Current Opinion in Obstetrics and Gynecology 1991, 3:470-476.

(Continued)

*Primary Examiner*—Sharon E. Kennedy
(74) *Attorney, Agent, or Firm*—TraskBritt (57) ABSTRACT

In one aspect, the present invention is directed to an osmotic pump that automatically provides an ascending release rate of active agent as the osmotic pump functions in an environment of operation and may be designed for implantation within a desired animal or human subject. An osmotic pump according to the present invention includes a reservoir, a rate controlling membrane, an expandable osmotic composition, an active agent formulation and an exit orifice. Once administered to an environment of operation, water passes through the rate controlling membrane and into the osmotic composition, which causes the osmotic composition to expand and expel the active agent formulation through the exit orifice at a rate that is directly proportional to the rate at which water passes through the rate controlling membrane. An osmotic pump according to the present invention permits the flow of water through the rate controlling membrane to increase automatically without the need for manipulation of the osmotic pump after administration. As the flow of water through the rate controlling membrane increases, the rate at which active agent is delivered from the osmotic pump will also increase proportionally.

17 Claims, 3 Drawing Sheets

U.S. PATENT DOCUMENTS

| | | |
|---|---|---|
| 5,997,527 A | 12/1999 | Gumucio et al. |
| 5,997,902 A | 12/1999 | Maruyama et al. |
| 6,113,938 A | 9/2000 | Chen et al. |
| 6,132,420 A | 10/2000 | Dionne et al. |
| 6,217,906 B1 | 4/2001 | Gumucio et al. |
| 6,245,357 B1 * | 6/2001 | Edgren et al. ............... 424/473 |
| 6,261,584 B1 | 7/2001 | Peery et al. |
| 6,270,787 B1 | 8/2001 | Ayer |
| 6,283,949 B1 | 9/2001 | Roorda |
| 6,287,295 B1 | 9/2001 | Chen et al. |
| 6,375,978 B1 | 4/2002 | Kleiner et al. |
| 6,436,091 B1 | 8/2002 | Harper et al. |
| 6,464,688 B1 | 10/2002 | Harper et al. |
| 6,471,688 B1 | 10/2002 | Harper et al. |
| 2001/0021822 A1 | 9/2001 | Ayer |
| 2001/0022974 A1 | 9/2001 | Ayer |
| 2003/0032947 A1 | 2/2003 | Harper et al. |

OTHER PUBLICATIONS

"Implantable infusion pumps: Technology poised for takeoff," BBI Newsletter, vol. 17, No. 12, pp. 209-211, Dec. 1994.

International Search Report dated Apr. 2005 (5 pages).

* cited by examiner

OSMOTICALLY DRIVEN ACTIVE AGENT DELIVERY DEVICE PROVIDING AN ASCENDING RELEASE PROFILE

CLAIM OF PRIORITY

Pursuant to the provisions of 35 U.S.C. 119(e), this application claims the benefit of the filing date of provisional patent application Ser. No. 60/507,920, filed Sep. 30, 2003, for "Osmotically Driven Active Agent Delivery Device Providing An Ascending Release Profile."

BACKGROUND

1. Field of the Invention

The present invention is directed to an osmotic pump capable of providing controlled delivery of a desired active agent. Specifically, the present invention includes an osmotic pump that is configured to automatically provide ascending release of active agent without the need for further manipulation of the osmotic pump after administration to an environment of operation.

2. State of the Art

The benefits provided by controlled delivery of active agents for the treatment of disease are well recognized in the art and various approaches have been taken to realize the goal of delivering active agents at desired rates over predetermined periods of time. One approach involves the use of implantable drug delivery devices. Controlled delivery of a beneficial agent from an implantable device over prolonged periods of time has several potential advantages. For instance, use of implantable delivery devices generally assures patient compliance, as implantable devices are not easily tampered with by the patient and can be designed to provide therapeutic doses of beneficial agent over periods of weeks, months, or even years without patient input. Moreover, because an implantable device may be placed only once during its functional life, implantable devices may offer reduced site irritation, fewer occupational hazards for patients and practitioners, reduced waste disposal hazards, decreased costs, and increased efficacy when compared to other parenteral administration techniques, such as injections, which require multiple administrations over relatively short time intervals.

Various different implantable controlled delivery devices are known in the art, and various different mechanisms have been employed for delivering active agent from implantable devices at a controlled rate over time. In one approach, implantable drug delivery devices are designed as diffusional systems. For example, subdermal implants for contraception that operate by diffusion are described by Philip D. Darney in Current Opinion in Obstetrics and Gynecology 1991, 3:470–476. In particular, the Norplant® system requires the placement of six levonorgestrel-filled silastic implants under the skin and provides protection from conception for up to five years. The Norplant® implants operate by simple diffusion, that is, the active agent diffuses through the polymeric material at a rate that is controlled by the characteristics of the active agent formulation and the polymeric material. In addition, Darney describes biodegradable implants, namely Capranor™ and norethindrone pellets. These diffusional systems are designed to deliver contraceptives for about one year and then dissolve. The Capranor™ systems consist of poly(ε-capralactone) capsules that are filled with levonorgestrel and the pellets are 10% pure cholesterol with 90% norethindrone.

Implantable infusion pumps represent another approach to the design of implantable devices capable of providing controlled release of active agents over prolonged periods of time. Such pumps have been described for delivering drugs by intravenous, intra-arterial, intrathecal, intraperitoneal, intraspinal and epidural pathways. Implantable infusion pumps are usually surgically inserted into a subcutaneous pocket of tissue in the lower abdomen. Exemplary regulator-type implantable pumps capable of constant flow, adjustable flow, or programmable flow of active agent formulations include pumps available from, for example, Codman of Raynham, Mass., Medtronic of Minneapolis, Minn.; and Tricumed Medinzintechnik GmbH of Germany. Further examples of implantable infusion pumps are described in U.S. Pat. Nos. 6,283,949; 5,976,109; and 5,836,935. Even further, implantable infusion pump systems for pain management, chemotherapy and insulin delivery are described in the BBI Newsletter, Vol. 17, No. 12, pages 209–211, December 1994. Implantable infusion pumps typically provide for more accurately controlled delivery than simple diffusional systems.

A particularly promising approach to controlled delivery of active agent from implanted devices involves osmotically driven devices. Such devices are typically simple in design, but capable of providing consistent and reproducible delivery of a range of active agents at a controlled rate over periods of days, weeks, months, or even years. Exemplary osmotic pumps that may be designed for implantation in a human or animal subject are described in, for example, U.S. Pat. Nos. 5,234,693; 5,279,608; 5,336,057; 5,728,396; 5,985,305; 5,997,527; 5,997,902; 6,113,938; 6,132,420; 6,217,906; 6,261,584; 6,270,787; 6,287,295; and 6,375,978, which are assigned to ALZA corporation of Mountain View, Calif., and are incorporated in their entirety herein by reference.

Implantable osmotic delivery devices are commonly referred to as "osmotic pumps" and typically include a reservoir, an expandable osmotic material, a drug formulation, and at least one delivery orifice. Where the expandable osmotic material and the drug formulation are formed of separate materials, the expandable osmotic material and the drug formulation may be separated by a member, such as a piston, which is movable within the reservoir. At least a portion of the reservoir included in an osmotic pump is generally semipermeable, allowing water to be taken into the system while working to prevent or minimize the undesired escape of materials forming the expandable osmotic material or the drug formulation from the reservoir. The osmotic material included in an osmotic pump typically draws water from the environment of operation into the osmotic pump through the semipermeable portion of the reservoir. As water is drawn into the device, and in particular into the osmotic material, the osmotic material expands and drug formulation is discharged through the delivery orifice of the osmotic pump at a chosen release rate or release rate profile.

Though they have proven useful for providing drug delivery at controlled rates, implantable osmotic pumps have been typically designed to provide substantially zero-order release rates of a desired active agent. However, there are instances where it would be desirable to provide an implantable, controlled release delivery device that delivers active agent at an ascending release rate after the device is introduced into a desired environment of operation. As it is used herein, the term "environment of operation" refers to any environment into which an osmotic pump can be introduced and is capable of supporting operation of the osmotic pump over a desired period of time. In particular, an implantable device that provides an ascending release rate of drug would be useful for the delivery of drugs that require an increase in dose over time in order to maintain efficacy or where the subject would benefit from a dosing regimen that starts with a relatively low initial dose but progresses to or terminates with a relatively higher dose of drug.

In U.S. Pat. Nos. 6,436,091; 6,464,688; and 6,471,688 and in U.S. Patent Application Publication 2003/0032947 A1, the contents of each of which are incorporated herein by reference, Harper et al. disclose implantable osmotic pumps that can be designed to allow the increase of the active agent release rate post implantation. However, the designs of the dosage forms described in these patent references are not without disadvantages. In particular, each of the designs disclosed in these references requires physical manipulation of the osmotic pump in order to increase the rate at which active agent is delivered post implantation. For example, the devices taught in U.S. Pat. Nos. 6,436,091; 6,464,688; and 6,471,688 include multiple rate controlling membranes, with one or more rate controlling membranes being initially sealed from permeation by aqueous fluid from the environment of operation. To increase the release rate provided by such devices, the seal formed over one or more of the initially sealed rate controlling membranes is breached by, for example, a lancet inserted within the subject. Alternatively, U.S. patent application Publication 2003/0032947 A1 teaches implantable osmotic pumps that incorporate the piercing mechanisms necessary to compromise the seals initially formed over one or more rate controlling membranes included in the devices. Though such a design does not require insertion of a lancet, the physical manipulation required to actuate the integrated piercing mechanisms may still result in patient discomfort and introduces an amount of uncertainty as to whether the implant has been properly manipulated to cause an increase in rate at which active agent is delivered.

It would be an improvement in the art, therefore, to provide an implantable osmotic pump that provides an ascending release rate of active agent without the need for further manipulation post implantation. In particular, it would be desirable to provide an implantable osmotic pump that automatically provides a desired ascending release rate profile post implantation. Ideally, the design of such a device would not only facilitate delivery of a wide range of active agents and active agent formulations, but would also enable the fabrication of implantable osmotic pumps providing a wide range of different ascending release rates.

SUMMARY OF THE INVENTION

In one aspect, the present invention is directed to an osmotic pump that automatically provides an ascending release rate of active agent as the osmotic pump functions in an environment of operation and may be designed for implantation within a desired animal or human subject. An osmotic pump according to the present invention includes a reservoir, a rate controlling membrane, an expandable osmotic composition, an active agent formulation and an exit orifice. Once administered to an environment of operation, water passes through the rate controlling membrane and into the osmotic composition, which causes the osmotic composition to expand and expel the active agent formulation through the exit orifice at a rate that is directly proportional to the rate at which water passes through the rate controlling membrane. To provide an ascending active agent release rate post implantation, an osmotic pump according to the present invention is designed such that the flow of water through the rate controlling membrane increases automatically without the need for manipulation of the osmotic pump after administration. As the flow of water through the rate controlling membrane increases, the rate at which active agent is delivered from the osmotic pump will also increase proportionally.

The design of the osmotic pump of the present invention is flexible, lending itself to the use of various different materials and configurations that provide different ascending release rate performance. For example, in one embodiment, the osmotic pump of the present invention is designed and configured to provide a release rate that increases with time throughout the functional life of the osmotic pump, while in another embodiment, the osmotic pump is designed and configured to provide an initial release rate for a desired period of time followed by an ascending release rate that increases throughout the remainder of the functional life of the osmotic pump. In yet a further embodiment, the osmotic pump of the present invention is designed and configured to provide an initial release rate for a desired period of time followed by an ascending release rate that increases over a second period of time to a final release rate that remains substantially constant for the remainder of the functional life of the osmotic pump. In yet a further embodiment, the osmotic pump of the present invention is designed and configured to provide an ascending release rate over an initial period of time and then remain substantially constant for the remainder of the functional life of the osmotic pump. As it is used herein, the term "functional life" refers to the period of time over which the osmotic pump of the present invention functions to deliver active agent at a desired rate.

The different components included in the osmotic pump of the present invention may be designed, configured or formulated in any manner that allows for the rate of water flow through the rate controlling membrane to increase to provide a desired ascending active agent release rate profile during the functional life of the osmotic pump. For example, in one embodiment of the osmotic pump of the present invention, the rate controlling membrane itself is designed or formulated to provide a membrane that exhibits a permeability that increases as the osmotic pump functions in an environment of operation. In another embodiment, the osmotic pump of the present invention includes a rate controlling membrane the exhibits a substantially constant permeability but is designed such that the surface area of the rate controlling membrane exposed to the environment of operation increases automatically as the osmotic pump functions. In yet another embodiment, the osmotic pump of the present invention includes a rate controlling membrane designed or formulated to exhibit a permeability that increases and is designed such that the surface area of the rate controlling membrane exposed to the environment of operation increases automatically as the osmotic pump functions. In a further embodiment, the osmotic pump of the present invention includes a rate controlling membrane that exhibits a substantially constant permeability but is designed such that the effective thickness of the rate controlling membrane can be decreased to, in turn, increase the release rate of the osmotic pump. In yet another embodiment, the osmotic pump of the present invention includes a rate controlling membrane designed or formulated to exhibit a permeability that increases and is designed such that the effective thickness of the rate controlling membrane can be decreased to, in turn, increase the release rate of the osmotic pump.

Where the osmotic pump of the present invention includes a rate controlling membrane exhibiting a permeability that increases as the osmotic pump functions (i.e., a rate increasing membrane), the rate controlling membrane may be configured or formulated using any suitable design or composition. In one embodiment, a rate increasing membrane is fabricated using a semipermeable material that itself exhibits an increase in permeability as the osmotic pump functions. In another embodiment, a rate increasing membrane included in an osmotic pump of the present invention is fabricated using a semipermeable material that exhibits a substantially constant permeability in combination with one or more permeation enhancing components having a permeability that increases as the osmotic pimp functions. Regardless of the specific embodiment, where the osmotic pump includes a rate increasing membrane, the configuration or formulation of the rate increasing membrane can be adjusted to allow fabrication of osmotic pumps providing a wide range of different ascending active agent release rate profiles.

In addition, various different pump configurations may be used to provide an osmotic pump that works to automatically increase the surface area of the rate controlling membrane exposed to an environment of operation. For example, the osmotic pump of the present invention may include a rate controlling membrane inserted within a reservoir, wherein at least a section of the wall forming the reservoir is formed of a degradable material that initially isolates a portion of the surface rate controlling membrane from exposure to aqueous fluids in the environment of operation. However, as the osmotic pump functions, environmental conditions cause the degradable section of the reservoir wall to degrade in a manner that increases the surface area of the rate controlling membrane exposed to water from the environment of operation. In one embodiment, the osmotic pump of the present invention includes a rate controlling membrane inserted into a reservoir, wherein the walls of the reservoir include at least one opening that is initially sealed by a buttplug formed by a material that degrades or erodes when exposed to the intended environment of operation. As the plug material degrades or erodes, additional surface area of the rate controlling membrane is exposed to water from the environment of operation causing the rate at which water passes through the rate controlling membrane to increase.

Furthermore, various different pump configurations may be used to provide an osmotic pump that works to automatically decrease the effective thickness of the rate controlling membrane, in turn, increase the release rate of the osmotic pump. For example, the osmotic pump of the present invention may include a rate controlling membrane inserted within a reservoir, wherein at least a section of the membrane is formed of a degradable material that initially contributes a portion of the thickness of the rate controlling membrane for the water permeation in the environment of operation. However, as the osmotic pump functions, environmental conditions cause the degradable section of the membrane to degrade in a manner that decreases the effective thickness of the rate controlling membrane for water to permeate from the environment of operation. In one embodiment, the osmotic pump of the present invention includes a rate controlling membrane inserted into a reservoir, wherein the membrane includes at least one portion that is initially filled by a plug formed by a material that degrades or erodes when exposed to the intended environment of operation. As the plug material degrades or erodes, the effective thickness of the rate controlling membrane is decreased for water to permeate, causing the rate at which water passes through the rate controlling membrane to increase.

DETAILED DESCRIPTION OF THE INVENTION

In one aspect, the present invention is directed to an osmotic pump that automatically provides an ascending release rate of active agent as the osmotic pump functions in an environment of operation and may be designed for implantation within a desired animal or human subject. As is illustrated in FIG. 1 through FIG. 10, an osmotic pump 10 according to the present invention includes a reservoir 12, an active agent formulation 14, an osmotic composition 16, a rate controlling membrane 22, a delivery orifice 24, and, optionally, a piston 26. Once administered to an environment of operation, water is drawn through the rate controlling membrane 22 and into the osmotic composition 16, which causes the osmotic composition 16 to expand and expel the active agent formulation 14 through the delivery orifice 24 at a rate corresponding to the rate at which water passes through the rate controlling membrane 22. To provide an ascending active agent release rate post implantation, an osmotic pump according to the present invention is designed such that the flow of water through the rate controlling membrane 22 increases automatically without the need for manipulation of the osmotic pump 10 after administration. As the flow of water through the rate controlling membrane 22 increases, the rate at which the active agent formulation 14 is expelled from the osmotic pump 10 also increases proportionally.

The reservoir 12 of the osmotic pump 10 of the present invention maybe sized and shaped as desired to suit a desired application or to facilitate placement of the osmotic pump 10 in a desired environment of operation. Materials suitable for forming the reservoir 12 must be sufficiently strong to ensure that the reservoir 12 does not leak, crack, break, or significantly distort under stresses to which it is subjected to during administration and operation of the osmotic pump 10. In particular, the reservoir 12 is formed of a material that is sufficiently rigid to withstand expansion of the osmotic composition 16 without undergoing substantial changes to the size or shape of the reservoir 12. The material used to form the reservoir 12 is also chosen to be largely impermeable to fluids from the environment of operation and to the material constituents included in the active agent formulation 14 and the osmotic composition 16. As it is used heroin the term "largely impermeable" indicates that the migration of materials into or out of the osmotic pump 10 through the material forming the reservoir 12 is so low that any such migration of materials has substantially no adverse impact on the function of the device.

The material used to form the reservoir 12 of an osmotic pump 10 according to the present invention is preferably not a bioerodible material and will remain intact even after the active agent formulation 14 has been delivered. Such a design facilitates recovery or passage of the osmotic pump 10 after the active agent formulation 14 contained therein has been delivered to or implanted within a subject. Typical materials suitable for the construction of the reservoir 12 of an osmotic pump 10 according to the present invention include, but are not limited to, non-reactive polymers and biocompatible metals and alloys. Specific examples of suitable polymers include, but are not limited to, polyimide, polysulfone, polycarbonate, polyethylene, polypropylene, polyvinylchloride-acrylic copolymer, polycarbonate-acrylonitrile-butadiene-styrene, polystyrene, acrylonitrile polymers, such as acrylonitrile-butadiene-styrene terpolymer and the like, halogenated polymers, such as polytetrafluoroethylene, polychlorotrifluorethylene, copolymer tetrafluorethylene and hexafluoropropylene. Metallic materials useful in forming the reservoir 12 include, but are not limited to, stainless steel, titanium, platinum, tantalum, gold, and their alloys, as well as gold-plated ferrous alloys, platinum-plated ferrous alloys, cobalt-chromium alloys, and titanium nitride coated stainless steel.

The osmotic composition 16 included in the osmotic pump 10 of the present invention may be formed of any material that creates sufficient osmotic pressure to draw water into the osmotic composition 16 through the rate controlling membrane 22 such that the osmotic composition 16 drives delivery of the active agent formulation 14 at a desired rate over a pre-selected period of time. Preferably, the osmotic composition 16 is formed as one or more osmotic tablets formed of an initially solid or non-flowable composition. However, the osmotic composition 16 included in an osmotic pump 10 according to the present invention is not limited to a tableted, and initially solid or non-flowable, composition. The osmotic composition 16 loaded into a reservoir 12 of an osmotic pump 10 according to the present invention may be formed in any suitable shape, texture, density, and consistency. For example, instead of a solid, tableted composition, it is possible that the osmotic composition 16 may be loaded into the reservoir 12 as a powdered material or a flowable gel.

The osmotic composition 16 includes an osmotic agent. The osmotic agent included in the osmotic composition 16 is a water-attracting agent that serves to draw water into the osmotic pump 10 through the rate controlling membrane 22, which drives the flow of active agent formulation 14 out from the osmotic pump 10. The osmotic agent is typically a water swellable or water soluble material capable of creating an osmotic pressure gradient and may include, for example, sugars, salts or an osmotic polymer. Methods and formulations for providing osmotic compositions 16 that are suitable for use in an osmotic pump 10 according to the present invention are well known. For example, U.S. Pat. Nos. 5,234,693; 5,279,608; 5,336,057; 5,728,396; 5,985,305; 5,997,527; 5,997,902; 6,113,938; 6,132,420; 6,217,906; 6,261,584; 6,270,787; 6,287,295; and 6,375,978, the contents of each of which are incorporated herein in their entirety by reference, detail methods and materials suitable for forming osmotic compositions 16 that may be used in an osmotic pump 10 according to the present invention. Specific examples of osmotic agents that may be useful in the osmotic composition 16 of an osmotic pump 10 of the present invention include, but are not limited to, magnesium sulfate, magnesium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides, and polysaccharides, such as sucrose, glucose, lactose, fructose, and dextran, as well as mixtures of any of these various species.

Osmotic polymers suitable for use in the osmotic composition 16 of osmotic pump 10 of the present invention include hydrophilic polymers that swell upon contact with water. Osmotic polymers may be natural (i.e., of plant or animal origin) or synthetic, and examples of osmotic polymers are well known in the art. Particular osmotic polymers that may be used in the osmotic composition 16 of an osmotic pump 10 of the present invention include, but are not limited to, poly(hydroxy-alkyl methacrylates) with molecular weights of 30,000 to 5,000,000, poly(vinylpyrrolidone) with molecular weights of 10,000 to 360,000, anionic and cationic hydrogels, polyelectrolyte complexes, poly(vinyl alcohol) having low acetate residual, optionally cross linked with glyoxal, formaldehyde or guiltaraldehyde and having a degree of polymerization of 200 to 30,000, a mixture of methyl cellulose, cross linked agar and carboxymethylcellulose, a mixture of hydroxypropyl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 80,000 to 200,000, Polyox Polyethylene oxide polymers having molecular weights of 10,000 to 5,000,000, starch graft copolymers, and Aqua-Keeps acrylate polymer polysaccharides.

In addition to an osmotic composition 16, an osmotic pump 10 according to the present invention may also include an additive or filler (not shown) distributed around the osmotic composition 16. The filler 28 used in an osmotic pump according to the present invention may be any flowable composition, such as a liquid or gel composition, which is substantially incompressible, suitable for use in the intended environment of operation and is compatible with the other components of the osmotic pump 10. Materials and methods suitable for providing a filler 28 suitable for use in an osmotic pump according to the present invention are also described in U.S. Pat. No. 6,132,420, the contents of which are herein incorporated in their entirety by reference.

Where it is included in an osmotic pump 10 according to the present invention, the filler 28 works to displace air or gas from around or within the osmotic composition 16, thereby working to reduce or eliminate start-up delays that can be caused by air entrapped within or around the osmotic composition 16 during the manufacturing process.

The inclusion of a filler 28 is particularly helpful where the osmotic composition 16 is formed of a tableted or powdered composition. The use of tableted and powdered osmotic compositions can result in the unwanted introduction of air or other compressible gas into the osmotic pump 10. For example, where a powdered osmotic composition is used, air may be entrapped within the osmotic composition or between the osmotic composition and the reservoir wall or, where included, the piston as the osmotic composition is filled within the reservoir. Moreover, where tableted osmotic compositions are used, air-filled gaps can be created between the osmotic composition and the reservoir or, where included, the piston. These air-filled gaps can result from the tableting and machining tolerances required to ensure placement of the osmotic composition within the reservoir. Even a small amount of entrapped air or other compressible gas within an osmotic pump according to the present invention can result in start-up delays. Air-filled gaps may also problematically affect the delivery rate of drug formulation when the osmotic pump is subjected to different external pressures, such as when a patient with an implanted osmotic pump scuba dives or travels to higher altitudes. The inclusion of a filler 28 serves to reduce or eliminate the extent to which any gaps around the osmotic composition 16 are filled with air or another gaseous material and, thereby, works to reduce or eliminate the delays and drug delivery inconsistencies that such gaps can produce.

The osmotic pump 10 of the present invention optionally includes a movable piston 18. Though optional, a movable piston 18 is particularly useful where the osmotic composition 16 and the active agent formulation 14 included in the osmotic pump 10 are provided by different materials or formulations. A movable piston 18 included in an osmotic pump 10 according to the present invention is configured to fit within the reservoir 12 in a sealed manner that allows the movable piston 18 to be displaced within the reservoir 12 as water is taken into the osmotic composition 16 and the osmotic composition 16 expands. In a preferred embodiment, a movable piston 18 is formed of a substantially non-compressible material. Moreover, a movable piston 18 suitable for use in an osmotic pump 10 of the present invention is preferably formed of a material that is impermeable to the osmotic composition 16 and the active agent formulation 14, and may include one or more protrusions, which work to form a seal between the movable piston 18 and the wall 20 of the reservoir 12. Materials suitable for use in a movable piston 18 included in an osmotic pump 10 of the present invention are known in the art and are described in, for example, U.S. Pat. Nos. 5,234,693; 5,279,608; 5,336,057; 5,728,396; 5,985,305; 5,997,527; 5,997,902; 6,113,938; 6,132,420; 6,217,906; 6,261,584; 6,270,787; 6,287,295, and 6,375,978, the contents of each of which are incorporated in their entirety herein by reference. Examples of materials that may be used to form a movable piston 18 useful in an osmotic pump 10 of the present invention include, but are not limited to, metallic materials, such as metal alloys, elastomeric materials, such as the non-reactive polymers already mentioned herein, as well as elastomers in general, such as polyurethanes, polyamides, chlorinated rubbers, styrene-butadiene rubbers, and chloroprene rubbers.

As can be seen by reference to the figures, the delivery orifice 24 included in an osmotic pump 10 of the present invention may simply include an orifice formed through one end of the wall 20 of the reservoir 12. Such a delivery orifice 24 can be provided using, for example, known molding methods or known mechanical or laser drilling methods. If desired, the reservoir 12 of an osmotic pump 10 of the present invention may include more than one delivery orifice 24. In an alternative embodiment, the delivery orifice 24 of an osmotic pump 10 of the present invention may be formed by an outlet plug (not illustrated) that is positioned at least partially within the reservoir 12. Such an outlet plug may be configured, for example, to provide a delivery orifice that optimizes flow of active agent formulation 14 or to regulate back diffusion of environmental fluids into the osmotic pump 10. Where the delivery orifice 24 of the osmotic pump 10 of the present invention is formed by an outlet plug, however, the outlet plug is prepared from a substantially non-compressible material. Outlet plugs suitable for application in an osmotic pump according to the present invention are known in the art and are described in, for example, U.S. Pat. Nos. 5,985,305; 6,217,906; and 5,997,527, the contents of each of which are herein incorporated in their entirety by reference. The dimensions of the delivery orifice 24, in terms of both diameter and length, will vary depending on, among other factors, the type of drug delivered, the rate at which the active agent formulation 14 is expelled from the osmotic pump 10, and the environment into which it is to be delivered.

The active agent included in the active agent formulation 14 contained within an osmotic pump 10 of the present invention can be present in a wide variety of chemical and physical forms. The osmotic pump 10 of the present invention is broadly applicable to the delivery of a wide variety of beneficial agents. Therefore, as it is used herein, the "active agent" refers to any beneficial agent that may be delivered to an environment of operation and includes, but is not limited to, medicaments, vitamins, nutrients, biocides, sterilization agents, food supplements, sex sterilants, fertility inhibitors, and fertility promoters. At the molecular level, the active agent may be present as an uncharged molecule, molecular complex, or pharmaceutically acceptable acid addition or base addition salts, such as hydrochlorides, hydrobromides, sulfate, laurylate, oleate, and salicylate. Salts of metals, amines or organic cations may be used for acidic active agent compounds. Derivatives of active agents, such as esters, ethers, and amides, can also be used. Moreover, the active agent formulation 14 included in an osmotic pump 10 according to the present invention may include more than one active agent, resulting in an osmotic pump 10 capable of delivering multiple drugs during its functional lifetime.

The active agent formulation 14 included in an osmotic pump 10 according to the present invention may include any formulation suitable for delivering a drug from an osmotic pump 10 according to the present invention. The active agent formulation 14 may be formulated as any flowable composition, such as a slurry, a suspension, or a solution, capable of delivering the desired active agent to a chosen environment of operation. As desired, the active agent formulation 14 included in an osmotic pump 10 according to the present invention may include one or more of various ingredients that work to allow delivery of the active agent to the desired environment of operation. In particular, the active agent formulation 14 included in an osmotic pump according to the present invention may optionally include preservatives, such as one or more antioxidants or other stabilizing agent, permeation enhancers, or carrier materials that are application appropriate. For example, if the osmotic pump is designed for implantation to a human or animal subject, any carrier, preservative, or permeation enhancer used would be a pharmaceutically acceptable material. Active agent formulations that may be used in an osmotic pump 10 according to the present invention include, but are not limited to, the formulations discussed in U.S. Pat. Nos. 5,234,693; 5,279,608; 5,336,057; 5,728,396; 5,985,305; 5,997,527; 5,997,902; 6,113,938; 6,132,420; 6,217,906; 6,261,584; 6,270,787; 6,287,295; and 6,375,978, the contents of each of which are incorporated in their entirety herein by reference.

The rate controlling membrane 22 included in an osmotic pump 10 according to the present invention defines the rate at which water enters the osmotic pump 10, and, as a result, controls the rate at which the active agent formulation 14 is delivered from the osmotic pump 10. In order to provide an ascending release rate, osmotic pump 10 of present invention is designed such that after the osmotic pump 10 has begun to function in an environment of operation, the rate at which water passes through the rate controlling membrane 22 increases to provide an ascending release rate of active agent formulation 14 from the osmotic pump 10.

A rate controlling membrane 22 of an osmotic pump 10 according to the present invention is sized and shaped for positioning within the reservoir 12. Preferably, the rate controlling membrane 22 is sized and shaped to form a tight interference fit with the wall 20 of the reservoir 12, acting like a cock or a stopper and obstructing and plugging the opening in the reservoir 12 within which the rate controlling membrane 22 is positioned. For example, where the reservoir 12 is substantially cylindrical in shape, the rate controlling membrane 22 will typically be cylindrical in shape and sized such that, once positioned within the reservoir 12, the rate controlling membrane 22 seals the interior of the reservoir 12 from the environment of operation and, except for the liquid required to drive the osmotic pump 10, prevents liquids and other substances from the environment of operation from entering the osmotic pump 10.

Though the reservoir 12 and rate controlling membrane 22 may be joined by any suitable method or mechanism, such as by an adhesive, threading mechanism, or other coupling device, the reservoir 12 and rate controlling membrane 22 are preferably configured such that the rate controlling membrane 22 is maintained in place throughout the operational life of the osmotic pump 10 through an interference fit created between the reservoir 12 and the rate controlling membrane 22. In order to ensure an interference fit that is sufficiently strong to withstand the operational stresses experienced by the rate controlling membrane 22 as the osmotic pump 10 operates, the rate controlling membrane 22 may be provided with one or more retaining means, such as one or more ribs (not illustrated) that extend away from the surface of the rate controlling membrane. U.S. Pat. Nos. 5,234,693; 5,279,608; 5,336,057; 5,728,396; 5,985,305; 5,997,527; 5,997,902; 6,113,938; 6,132,420; 6,217,906; 6,261,584; 6,270,787; 6,287,295; and 6,375,978, the contents of each of which are incorporated herein in their entirety by reference, teach various different rate controlling membrane configurations, including ribbed rate controlling membranes, that may be used in an osmotic pump 10 according to the present invention.

A rate controlling membrane 22 included in an osmotic pump 10 of the present invention includes a semipermeable material. The semipermeable material used in the rate controlling membrane 22 allows liquids, particularly water, to pass from an the environment of operation into the osmotic composition 16 contained within the reservoir 12, causing the osmotic composition 16 to swell. However, the semipermeable material included in the rate controlling membrane 22 is largely impermeable to the materials within the reservoir 12 and other matter included in the environment of operation. Materials suitable for use in formulating the semipermeable material of a rate controlling membrane 22 included in an osmotic pump 10 according to the present invention are taught, for example, in U.S. Pat. Nos. 4,874,388; 5,234,693; 5,279,608; 5,336,057; 5,728,396; 5,985,305; 5,997,527; 5,997,902; 6,113,938; 6,132,420; 6,217,906; 6,261,584; 6,270,787; 6,287,295; and 6,375,978, the contents of each of which are incorporated herein in their entirety by reference.

Theoretically, the liquid permeation rate dV/dt through a rate controlling membrane 22 included in an osmotic pump 10 of the present invention is equal to the liquid permeability coefficient P for the membrane forming material multiplied by the exposed surface area of the membrane A and the osmotic pressure difference $\Delta\pi$ generated between the interior of the reservoir 12 and the environment of operation by the osmotic composition 16, divided by the thickness of the membrane sheet L.

$$dV/dt = P\,A\Delta\pi/L$$

The active agent delivery rate dMt/dt is theoretically equal to the liquid permeation rate dV/dt multiplied by the concentration C of the beneficial agent.

$$dMt/dt = dV/dt \cdot C = \{P\,A\Delta\pi/L\} \cdot C$$

Therefore, even where $\Delta\pi$ and C remain the same, the active agent delivery rate provided by the osmotic pump 10 of the present invention can be increased by increasing A (the amount of surface area of the rate controlling membrane 22 exposed), L (effective thickness of the rate controlling membrane 22), or P (the liquid permeability coefficient of the membrane forming material), or any of those combinations.

Figure 1:
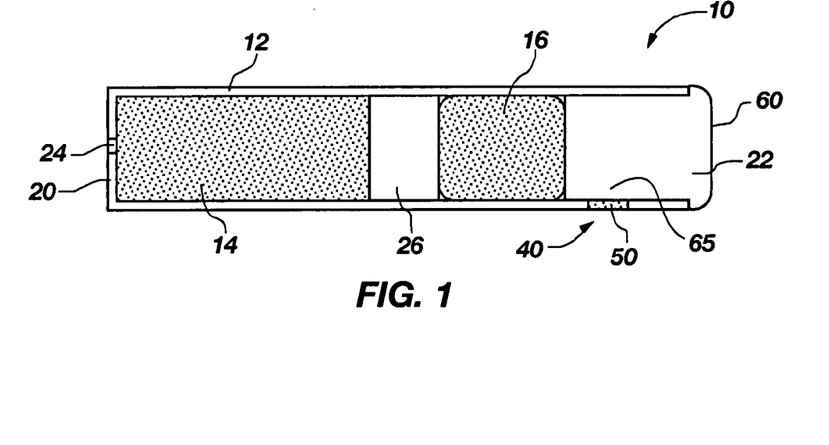
FIG. 1 and FIG. 2 provide schematic, cross-sectional representations of a first embodiment of an osmotic pump according to the present invention.
Figure 2:
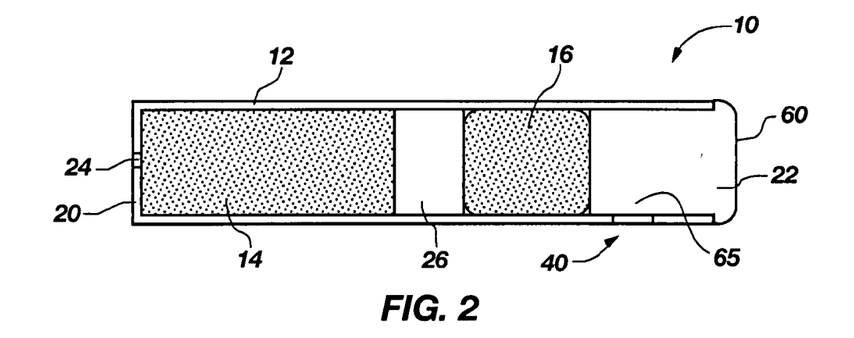
Figure 3:
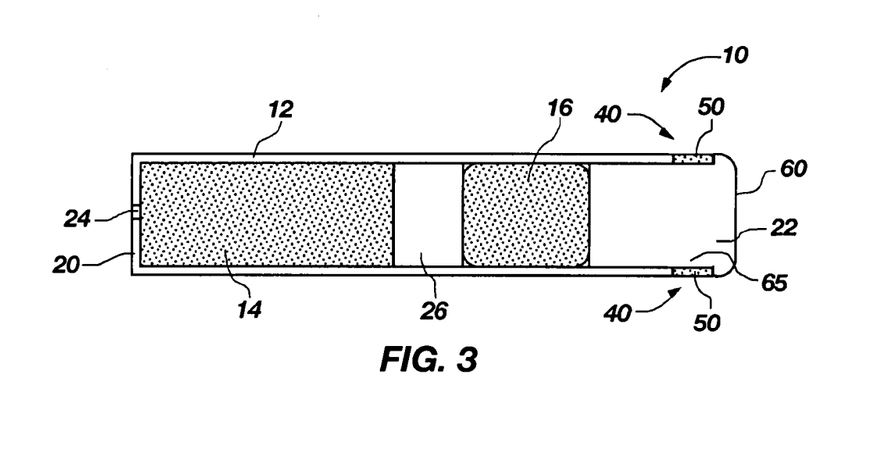
FIG. 3 and FIG. 4 provide schematic, cross-sectional representations of a second embodiment of an osmotic pump according to the present invention.
Figure 4:
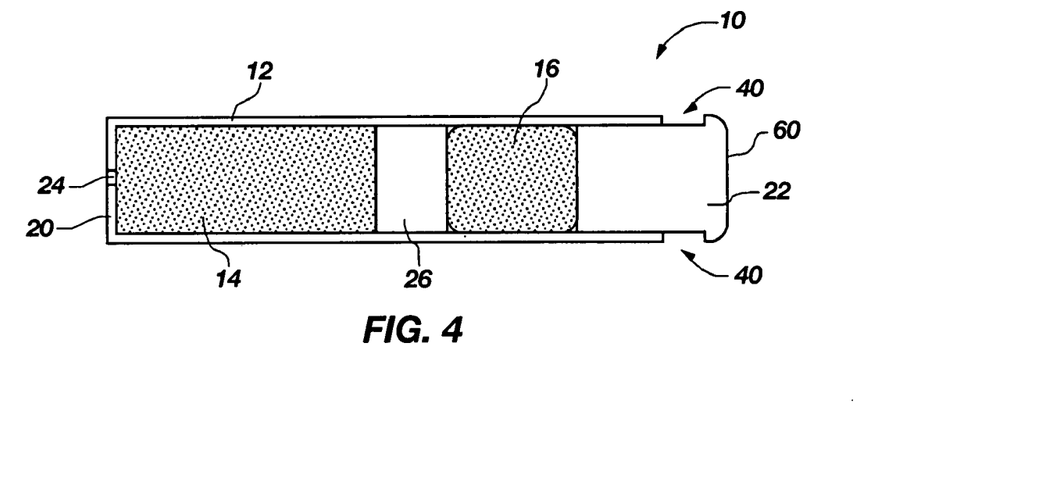
Figure 5:
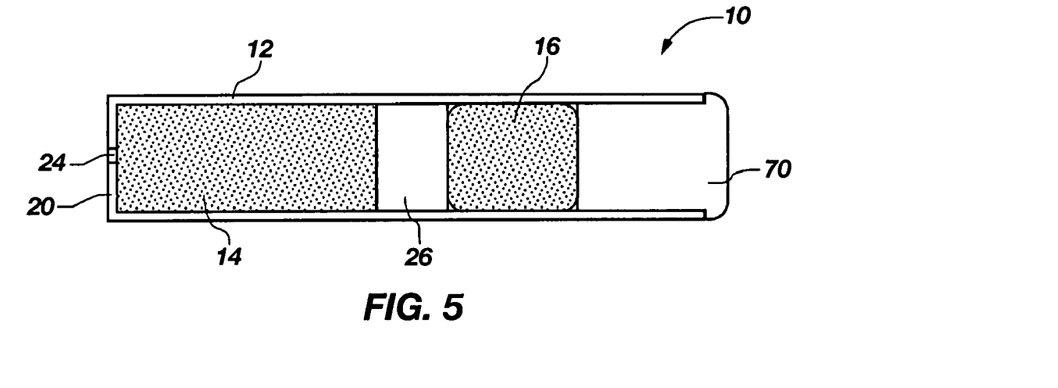
FIG. 5 through FIG. 10 provide schematic, cross-sectional representations of various different embodiments of an osmotic pump including a rate increasing membrane according present invention.
Figure 6:
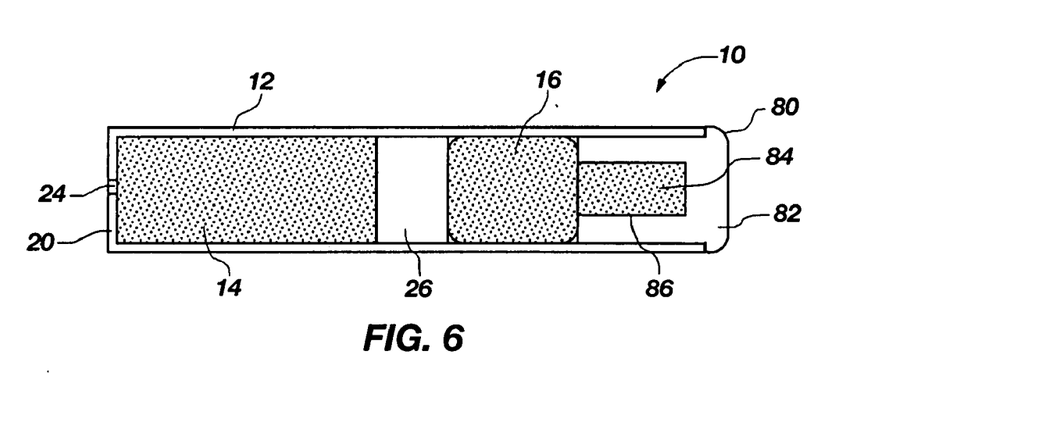
Figure 7:
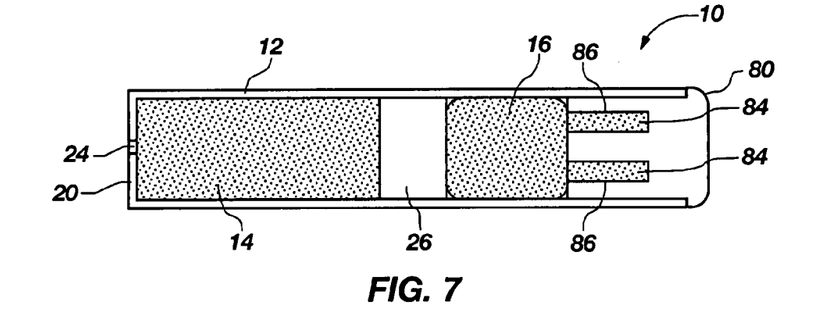
Figure 8:
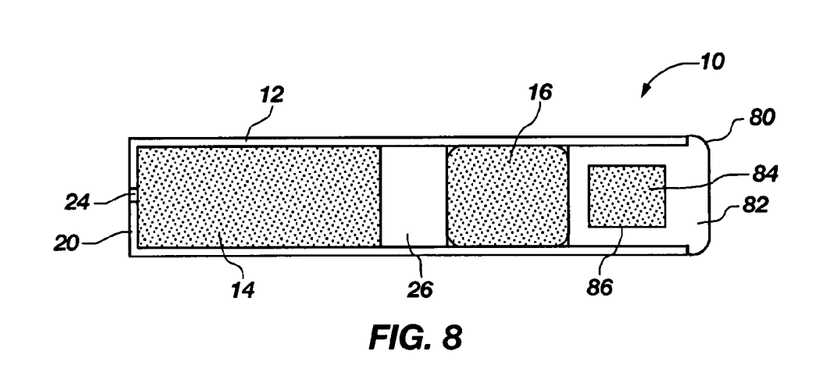

In one embodiment, the osmotic pump 10 of the present invention is designed such that, as the osmotic pump 10 operates, the surface area of rate controlling membrane 22 exposed to the environment of operation automatically increases. For example, as is shown in FIG. 1 and FIG. 3, the reservoir 12 included in the osmotic pump 10 of the present invention may include an open section 40 of wall 20 of reservoir 12 that is initially sealed by a temporary seal 50 formed of a material that degrades, such as by hydrolysis, dissolution, or erosion, in the intended environment of operation. When the rate controlling membrane 22 is positioned within the reservoir 12, a first area 60 of the rate controlling membrane 22 is left exposed to the environment of operation and the open section 40 of the reservoir 12 is positioned over a second area 65 of the rate controlling membrane 22. The temporary seal 50 included in the open section 40 of the reservoir 12 initially isolates the second area 65 of the rate controlling membrane 22 from direct contact by material from the environment of operation through the open section 40. As the osmotic pump 10 functions in the environment of operation, however, the conditions present in environmental conditions cause the material forming the temporary seal 50 to degrade such that liquid from the environment of operation can directly contact the second area 65 of the rate controlling membrane 22 through the open section 40 of the reservoir 12 (shown in FIG. 2 and FIG. 4). Therefore, as the temporary seal 50 included in the open section 40 of the reservoir 12 degrades, the exposed surface area of the rate controlling membrane 22 automatically increases, causing an increase in the rate at which water passes through the rate controlling membrane 22 and a corresponding increase in the active agent delivery rate without the need for physical manipulation of the osmotic pump 10.

The temporary seal 50 may be formed using conventional techniques, such as a suitable melt fill, molding or compression techniques. Moreover, the temporary seal 50 may be created using any degradable material that is compatible with the remaining components of the osmotic pump 10, is capable of initially sealing the open section 40 of the reservoir 12, and breaks down over a desired period of time in an intended environment of operation to expose the second area 65 of the rate controlling membrane 22 to direct contact by liquid material from the environment of operation through the open section 40. The degradable material forming the temporary seal 50 may break down through a variety of mechanisms. For example, the degradable material may be formulated to melt, dissolve, erode, or hydrolyze in the intended environment of operation over a desired period of time to produce a desired ascending active agent release rate.

Specific materials that may be used to form the temporary seal 50 include Poly-Lactic-Co-Glycolic Acid (PLGA), PLGA-like materials, and Lauryl Lactate-Polyvinyl-Pyrrolidone. The degradable material used to create the temporary seal 50 included in an osmotic pump 10 according to the present invention are preferably formulated to degrade to such an extent that liquid permeability of any material remaining within the open section 40 is significantly greater than the liquid permeability of the rate controlling membrane 22.

Where the osmotic pump 10 of the present invention includes a reservoir 12 having an open section 40 with a temporary seal 50, the timing and rate at which the active agent release rate provided by the osmotic pump 10 ascends can be controlled by altering the formulation of the degradable material forming the temporary seal 50. For example, where the degradable material is designed to dissolve in the environment of operation, materials having various solubilities or dissolution rates may be selected or combined to provide a temporary seal that dissolves over a desired period of time. In addition, the degradable material forming the temporary seal 50 may be formed of different layers of materials that provide different degradation characteristics. A delay in the ascent of the active agent release rate profile can be simply achieved by forming the temporary seal of a material that will not substantially degrade over a period of time that allows for the desired delay. Using the teachings provided herein, one of skill in the art can select and formulate the materials used to form the temporary seal 50 to achieve a seal that degrades over a desired period of time to provide a targeted ascending active agent release rate profile.

Moreover, where an osmotic pump 10 according to the present invention includes an open section 40 sealed by a temporary seal 50, the extent to which the release rate of the osmotic pump 10 increases can also be adjusted by altering the size, number or location of the open sections 40 included in the reservoir 12. As the amount of surface area of the rate controlling membrane 22 exposed by the open sections 40 provided in the reservoir 12 increases, the increase in release rate provided as the temporary seal 50 degrades becomes greater. Therefore, if a larger increase in active agent release rate is desired, open sections 40 included in the reservoir 12 should be designed to expose a larger surface area of the rate controlling membrane 22. For example, because the open section 40 provided in the reservoir 12 of the osmotic pump 10 illustrated in FIG. 3 is relatively larger than the open section 40 provided by the reservoir 12 of the osmotic pump 10 illustrated in FIG. 1, the osmotic pump 10 illustrated in FIG. 3 will provided a relatively larger increase in active agent release rate as the temporary seal 50 degrades. An osmotic pump 10 according to the present invention may include one or more open sections 40 sized and shaped to provide a wide range of active agent release rates.

In addition, the liquid permeation rate of the rate controlling membrane 22 included in an osmotic pump 10 of the present invention is also affected by the longitudinal position of the open sections 40 provided in the reservoir 12. The shorter the distance that the liquid must travel through the membrane, the faster the liquid will permeate the rate controlling membrane 22. Accordingly, the closer the open sections 40 are to the end of the membrane plug 26 adjacent to osmotic composition 16, the faster liquid from the environment of operation will enter the osmotic composition 16 and the faster the active agent composition will be released from the osmotic pump 10. Therefore, a relatively greater increase in active agent release rate can be achieved in an osmotic pump 10 according to the present invention by positioning one or more open sections 40 such that they are relatively closer to the end of the rate controlling membrane 22 adjacent the osmotic composition 16.

As can be seen from the foregoing, the increase in liquid permeation rate and thus, the beneficial agent delivery rate provided by an osmotic pump 10 according to the present invention can be controlled by changing the surface area of the rate controlling membrane 22 exposed by open sections 40 provided in the reservoir 12 without the need to change the overall geometry of the pump device 10 or the rate controlling membrane 22. The increase in delivery rate can also be controlled by varying the longitudinal position of the open sections 40.

In another embodiment, the osmotic pump 10 of the present invention achieves an ascending active agent release rate through the use of a rate controlling membrane that exhibits a permeability that automatically increases as the osmotic pump 10 functions in an environment of operation. As can be appreciated by reference to FIG. 5 through FIG. 10, such rate increasing membranes 70, 80 may be formed in a variety of configurations. In each configuration, however, a rate increasing membrane 70 according to the present invention exhibits a permeability that automatically increases during the operational life of the osmotic pump 10 such that a desired ascending active agent release rate is achieved.

In a first configuration (shown in FIG. 5), the rate increasing membrane 70 includes a single material formulated to increase in permeability as the osmotic pump 10 functions in an environment of operation. In order to achieve such membrane formulation, a rate increasing membrane 70 may be formulated of one or more semipermeable materials that exhibit an increase in permeability as the osmotic pimp 10 functions in an environment of operation. For example, the semipermeable material used to form the rate increasing membrane 70 may be relatively hydrophobic when first administered to the environment of operation, exhibiting a relatively lower liquid permeability. However, as the osmotic pump 10 functions in the environment of operation, material forming the rate increasing membrane 70 may be formulated to undergo a chemical change, such as a by hydrolysis, that renders the material more hydrophilic over a period of time and results in a rate controlling membrane that is increasingly permeable to liquid from the environment of operation.

As is shown in FIG. 6 through FIG. 10, a rate increasing membrane 70 suitable for providing an osmotic pump 10 according to the present invention may also be fabricated as a compound membrane 80 formed of a semipermeable material 82 and a permeability enhancing material 84, wherein the two different materials exhibit different permeability characteristics. The semipermeable material 82 is largely impermeable to the materials contained within the reservoir 12 and the compound membrane 80 is configured such that the semipermeable material 82 isolates the contents of the reservoir 12 from the environment of operation and largely prevents migration of material from within the reservoir 12 into the environment of operation through the compound membrane 80. The permeability enhancing material 84 included in a compound membrane 80 according to the present invention is fabricated to provide an initial permeability that is less than the initial permeability of the semipermeable material 82. However, as the osmotic pump 10 operates, the permeability enhancing material 84 is fabricated such that the permeability of the permeability enhancing material 84 increases. In a preferred embodiment, the permeability enhancing material 84 is fabricated such that permeability of the permeability enhancing material 84 becomes greater that the permeability of the semipermeable material 82 included in the compound membrane 80. Though the permeability enhancing material 84 included in a compound membrane 80 of the present invention may be semipermeable, the permeability enhancing material 84 need not exhibit semipermeable characteristics.

Figure 9:
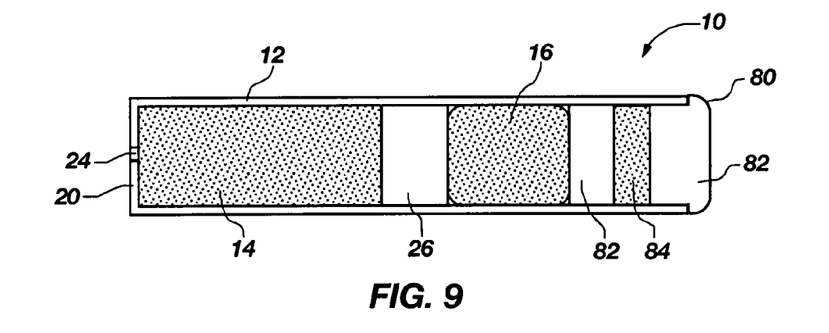
Figure 10:
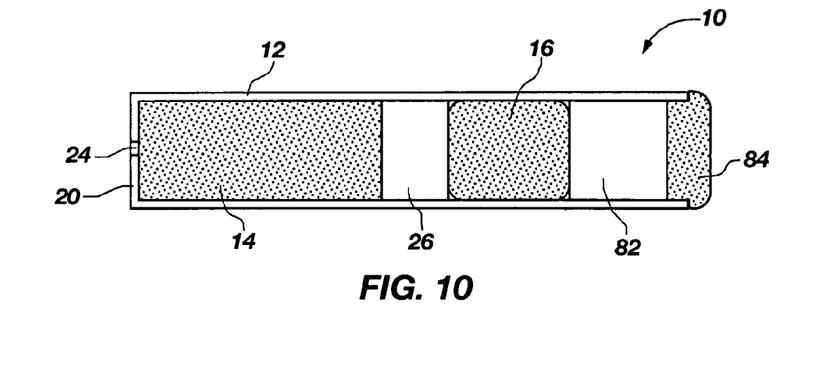

As is easily appreciated by reference to FIG. 6 through FIG. 10, a compound membrane 80 according to the present invention can be fabricated in any suitable configuration. For example, a compound membrane 80 may include a semipermeable material 82 formed to accept one or more inserts 86 of various shapes or sizes formed of the permeability enhancing material 84 (shown in FIG. 6 through FIG. 8). Alternatively, as can be seen in FIGS. 9 and 10, a compound membrane 80 according to the present invention may be formed by a laminated structure, wherein one or more layers are formed by the semipermeable material 82 and one or more layers are formed by the permeability enhancing material 84. Though a compound membrane 80 according to the present invention may be fabricated such that the permeability enhancing material 84 is in direct contact with the environment of operation, as is shown in FIG. 10, it is preferred that the permeability enhancing material 84 be isolated from the environment of operation by the semipermeable material 82. Where the permeability enhancing material 84 is isolated from the environment of operation, as is illustrated in FIG. 6 through FIG. 9, any degradation products formed as the permeability of the permeability enhancing material 84 increases can be substantially maintained within the reservoir 12 of the osmotic pump 10 and do not enter the environment of operation.

In another embodiment, the compound membrane 80 shown in FIG. 10 can be modified by substituting the permeability enhancing material 84 with a material that degrades, such as by hydrolysis, dissolution, or erosion, in the intended environment of operation (e.g., through use of materials such as those used to form temporary seal 50, as previously described). Thus, the osmotic pump 10 includes a compound membrane 80 inserted into a reservoir 12, wherein the membrane includes at least one portion (identified as portion 84 in FIG. 10) that is initially filled by a plug formed by a material that degrades or erodes when exposed to the intended environment of operation. As the plug material degrades or erodes, the effective thickness of the rate controlling membrane 80 is decreased for water to permeate, causing the rate at which water passes through the rate controlling membrane 80 to increase.

The semipermeable material 82 included in a compound membrane 80 according to the present invention may include any of the semipermeable materials already detailed herein. For example, the semipermeable material 82 included in a compound membrane 80 may be formed using the semipermeable materials described in U.S. Pat. Nos. 4,874,388; 5,234,693; 5,279,608; 5,336,057; 5,728,396; 5,985,305; 5,997,527; 5,997,902; 6,113,938; 6,132,420; 6,217,906; 6,261,584; 6,270,787; 6,287,295; and 6,375,978, the contents of each of which are incorporated in their entirety herein by reference. Specific examples of semipermeable materials suitable for forming the semipermeable material 82 included in a compound membrane include, but are not limited to, Hytrel polyester elastomers (DuPont), cellulose esters, cellulose ethers and cellulose ester-ethers, water flux enhanced ethylene-vinyl acetate copolymers, semipermeable membranes made by blending a rigid polymer with water-soluble low molecular weight compounds, and other semipermeable materials well known in the art. The above cellulosic polymers have a degree of substitution on the anhydroglucose unit, from greater than 0 up to 3 inclusive. By, "degree of substitution," or "D.S.," is meant that the average number of hydroxyl groups originally present on the anhydroglucose unit comprising the cellulose polymer that are replaced by a substituting group. Representative materials include, but are not limited to, one selected from the group consisting of cellulose acylate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D.S. of 1.8, and acetyl content of 4% average weight percent and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like. Other semipermeable materials suitable for use in a semipermeable material 82 according to the present invention include, polyurethane, polyetherblockamide (PEBAX, commercially available from ELF ATOCHEM, Inc.), injection-moldable thermoplastic polymers with some hydrophilicity such as ethylene vinyl alcohol (EVA).

A wide variety of materials may be used to form the permeability enhancing material 84 included in a semipermeable material 82 according to the present invention. For example, the permeability enhancing material 84 may itself be semipermeable in nature, but the permeability enhancing material 84 need not be semipermeable, or it may be much less permeable than semipermeable material 82 initially. Preferred materials for creating the rate increasing membranes include water-soluble materials, water degradable materials, and other biodegradable materials. For example, the rate increasing membrane may be formed using an osmagent as well as water soluble and biodegradable polymers. Where the permeability enhancing material 84 is formed using water-soluble materials, as the osmotic pump 10 functions and water passes through the compound membrane 80, the water soluble materials will dissolve or elute out of the compound membrane 80, allowing for an increase in membrane permeability. However, the material forming the permeability enhancing material 84 need not be water soluble, but may also be chosen to degrade via any mechanism that allows the permeability of the compound membrane 80 to increase as the osmotic pump 10 functions. For example, the permeability enhancing material 84 may include a material that degrades by becoming more hydrophilic, such as by hydrolysis, as it is exposed to aqueous liquid from the environment of operation and the osmotic pump 10 functions. Alternatively, the permeability enhancing material 84 may include a material that simply erodes or dissolves as the osmotic pump 10 functions such that the permeability of the compound membrane 80 increases.

Osmotic agents that may be useful in forming a permeability enhancing material 84 include, but are not limited to, osmotic polymers, such as those described herein, magnesium sulfate, magnesium chloride, sodium sulfate, sodium chloride, lithium sulfate, sodium phosphate, potassium phosphate, d-mannitol, sorbitol, inositol, urea, magnesium succinate, tartaric acid, raffinose, and various monosaccharides, oligosaccharides, and polysaccharides, such as sucrose, glucose, lactose, fructose, and dextran, as well as mixtures of any of these various species. The permeability enhancing material 84 may be formed solely by an osmotic agent or an osmotic agent may be combined with one or more additional materials to achieve a permeability enhancing material 84 that achieves permeability characteristics that are different from those achievable from using an osmagent alone. Where the permeability enhancing material 84 is formed using one or more osmotic agents, the permeability enhancing material 84 may be formed, for example, by known tableting, molding, or casting techniques.

The permeability enhancing material 84 included in a compound membrane 80 useful in an osmotic pump 10 according to the present invention may also be formed using polymer materials that are not necessarily osmotic agents. Polymer materials that may be used to form the permeability enhancing material 84 include, but are not limited to, biodegradable polylactides, polyglycolides, polycaprolactones, polyanhydrides, polyorthoester, polydioanones, polyacetals, polyketals, polycarbonates, polyphosphoesters, polyorthocarbonate, polyphosphazenes, and polyurethanes. Preferred polymer materials useful for forming the permeability enhancing material 84 include polylactides, polyglycolides, copolymers of lactide and glycolide, and polyurethanes including a soft segment that is hydrolysable. Where the permeability enhancing material 84 includes a polyurethane having a hydrolysable soft segment, the soft segment can include, for example, a polycaprolactone, a copolymer of polycaprolactone with a polylactic acid or a polyglycolic acid, or a mixture of polycaprolactone or a copolymer of polycaprolactone with polyethylene glycol (the polyethylene glycol working to further control the initial hydrophobicity of the permeability enhancing material 84). The permeability enhancing material 84 may be formed solely of polymer material. Alternatively, the permeability enhancing material 84 may be formed by combining a polymer material, such as those described herein, with one or more different materials, such as an osmotic agent, to provide a permeability enhancing material 84 exhibiting permeability characteristics not achievable by polymer materials alone.

The permeability enhancing material 84 may also be formed of a matrix material that includes a substantially non-degradable material along with material that degrades as the osmotic pump functions. For example, a matrix formed of a porous material that is mixed, coated, filled or infused with a degradable material may be used to form the permeability enhancing material 84 of a compound membrane 80 according to the present invention. Where a porous material is used to form the permeability enhancing material 84 of a compound membrane 80, the porous material is preferably selected such that it does not substantially degrade as the osmotic pump 10 functions. Examples of porous materials that may be used to create a rate-increasing matrix include, but are not limited to, metals, glasses, and plastics that are fashioned with pores, holes, or liquid permeable channels. Preferred porous materials forming a rate-increasing matrix include fritted glass or metal and macroporous polymer materials. To complete a rate increasing matrix useful as the permeability enhancing material 84 of a compound membrane 80 of the present invention, a degradable material, such as an osmagent, water soluble polymer, biodegradable polymer, or a combination of such materials, is coated on, mixed with, or dispersed or infused within the porous material. The degradable material included in rate-increasing matrix may include any water-soluble, water degradable, or biodegradable material that is compatible with porous material, the semipermeable material 82 and the remaining components of the osmotic pump. For example, the degradable material may be formed using one or more of the water soluble, water degradable, or biodegradable materials already described herein.

Where the permeability enhancing material 84 is formed as an insert 86, the insert 86 may be formed in any number of different shapes and sizes, but preferably matches the size and shape of a hollow interior portion formed within the semipermeable material 82 of the compound membrane 80. Therefore, an insert 86 of permeability enhancing material 84 is typically sized and shaped to be matingly received within a hollow interior portion formed within the semipermeable material 82. Moreover, the material used to form an insert 86 may work in concert with the semipermeable material 82 to form a compound membrane 80 that remains sufficiently structurally stable to effect and maintain a tight interference fit with the wall 20 of the reservoir 12 throughout the functional life of the osmotic pump 10.

An insert 86 of permeability enhancing material 84 included in a compound membrane 80 of the present invention may be manufactured and positioned within an appropriate hollow interior portion of the semipermeable material 82 using any suitable method. For example, the insert 86 may be first manufactured, and then inserted within a hollow interior portion of the semipermeable material 82 manually or using a known insertion device providing insertion depth or insertion force control. Where the insert is manufactured prior to positioning within a hollow interior portion of the semipermeable material 82, the any suitable manufacturing technique, such as known extrusion, casting, compression, or injection molding techniques, may be used to produce the insert. Even where the insert is formed as a matrix material, the matrix may be manufactured through known casting, extrusion, injection molding, or liquid or melt fill processes. For example, the degradable material may be imbedded into the porous material included in the matrix by dissolving the degradable material in a solvent, filling the solution into the porous material and removing the solvent.

Where the osmotic pump 10 according to the present invention includes a compound membrane that includes one or more inserts, the release rate characteristics provided by the compound membrane can be altered to provide desired adjustments in the active agent release rate profiled by altering the characteristics of the one or more inserts. For example, where the osmotic pump 10 of the present invention is configured to provide a first substantially constant release rate, followed by an ascending release rate, followed by a second substantially constant release rate, the difference between the first and second substantially constant release rates can be adjusted by altering the length of the one or more inserts included. As the length of the inserts increase, the difference between the first and second substantially constant release rates will also increase. Moreover, where a compound membrane according to the present invention includes one or more inserts of permeability enhancing material, the time required to ramp up from a first release rate to a second release rate can be adjusted by altering the length of the one or more inserts included, with longer inserts typically providing faster ascending release rates.

Even where the length of an insert included in a compound membrane according to the present invention is constant, the ascending release rate provided by the compound membrane can be adjusted by altering the chemical composition of the permeability enhancing material forming the insert. For instance, the slower the permeability enhancing material degrades, the slower the release rate will ascend. The converse is also true; as the permeability enhancing material is formulated to degrade more rapidly, the release rate provided by compound membrane will ascend more rapidly. The chemical composition of the permeability enhancing material included in a compound membrane typically controls the degradation rate of the permeability enhancing material. For example, if polylactide (PLA) or PLGA is used as the permeability enhancing material, the degradation rate of PLGA will typically be higher than the degradation rate of PLA. Further, adjusting the amounts of the constituents included in a co-polymer compound can alter the degradation rate. The degradation rate of PLGA (L/G 85/15) will typically be lower than the degradation rate of PLGA (L/G 75/25), which will typically be lower than the degradation rate of PLGA (L/G 50/50). Even further, where the same PLGA is used, higher molecular weight PLGA materials will provide slower degradation rates than lower molecular weight PLGA materials.

Of course, an osmotic pump according to the present invention can also include a permeability enhancing membrane in combination with a reservoir that includes an open section of wall that is initially sealed by a temporary seal formed of a material that degrades, as described herein. The rate of delivery of active agent from such an osmotic pump would increase as the pump functions due to both an increase in permeability of the rate increasing membrane and in increase in the surface area of the rate increasing membrane exposed to water from the environment of operation. A design including both a rate increasing membrane and a reservoir including an open section that is initially sealed may achieve an ascending release rate that would not otherwise be readily achieved.

An osmotic pump according to the present invention may be designed to provide a variety of different ascending release profiles. In one embodiment, the osmotic pump of the present invention is characterized by an active agent release rate that increases over the entire functional life of the osmotic pump. In another embodiment, the osmotic pump of the present invention is characterized by an initial, substantially constant active agent release rate that is maintained for a first period of time, followed by a subsequent active agent release rate that ascends over a second period of time. In yet another embodiment, the osmotic pump of the present invention is characterized by an initial, substantially constant active agent release rate, followed by a subsequent ascending active agent release rate, with the ascending active agent release rate being followed by a final, substantially constant active agent release rate that is greater than the initial, substantially constant active agent release rate.

Although osmotic pumps according to the present invention are preferably designed administered to human or animal physiological environments, osmotic pumps according to the present invention are generally applicable for the delivery of beneficial agents to an environment of operation and are not limited in utility to physiological environments. For example, the osmotic pumps according to the present invention may be used in intravenous systems (e.g. attached to an IV pump, and IV bag, or an IV bottle) for delivering beneficial agents to animals or humans, systems for blood oxygenation, kidney dialysis or electrophoresis, systems for delivering, for instance, nutrients or growth regulating compounds to cell cultures, as well as in pools, tanks, reservoirs and the like.

What is claimed is:

1. An osmotic pump that automatically provides an ascending release rate of active agent comprising:
    a reservoir having an opening at a first end and a delivery orifice at a second end;
    a rate controlling member coupled to the first end of the reservoir, wherein the rate controlling member comprises a semipermeable material having a substantially constant fluid permeability and at least one permeation enhancing material having an increasing fluid permeability and wherein the semipermeable material is formed to accept one or more inserts formed of the permeability enhancing material;
    an osmotic composition that expands at a rate proportional to the rate at which fluid passes through the rate controlling member, the osmotic composition located inside the reservoir; and
    an active agent formulation in fluid communication with the delivery orifice.

2. The osmotic pump of claim 1, wherein the rate controlling member has a fluid permeability rate that increases with time.

3. The osmotic pump of claim 1, wherein the one or more inserts of permeability enhancing material are sized and shaped to be received within a hollow interior portion formed within the semipermeable membrane.

4. The osmotic pump of claim 1, wherein the semipermeable material is selected from the group consisting of polyester elastomers, cellulose esters, cellulose ethers and cellulose ester-ethers, water flux enhanced ethylene-vinyl acetate copolymers, and mixtures thereof.

5. The osmotic pump of claim 1, wherein the permeability enhancing material is selected from the group consisting of osmotic agents, water-soluble materials, water degradable materials, and biodegradable materials.

6. The osmotic pump of claim 1, wherein the permeability enhancing material is selected from the group consisting of magnesium sulfate, magnesium chloride, sodium sulfate, sodium chloride, lithium sulfate, sodium phosphate, potassium phosphate, d-mannitol, sorbitol, inositol, urea, magnesium succinate, tartaric acid, raffinose, monosaccharides, oligosaccharides, polysaccharides, and mixtures thereof.

7. The osmotic pump of claim 1, wherein the permeability enhancing material is selected from the group of polymer materials consisting of biodegradable polylactides, polyglycolides, polycaprolactones, polyanhydrides, polyorthoester, polydioanones, polyacetals, polyketals, polycarbonates, polyphosphoesters, polyorthocarbonate, polyphosphazenes, polyurethanes, and copolymers of lactide and glycolide.

8. The osmotic pump of claim 1, wherein the permeability enhancing material comprises a polyurethane having a hydrolysable soft segment.

9. The osmotic pump of claim 8, wherein the hydrolysable soft segment is selected from the group consisting of a polycaprolactone, a copolymer of polycaprolactone with a polylactic acid, a copolymer of polycaprolactone with a polyglycolic acid, and a mixture of polycaprol actone with polyethylene glycol.

10. The osmotic pump of claim 1, wherein the permeability enhancing material comprises a matrix material having a porous material and a degradable material.

11. The osmotic pump of claim 1, further comprising a movable piston located between the osmotic composition and the active agent formulation.

12. The osmotic pump of claim 1, wherein the osmotic composition is selected from the group consisting of an osmotic agent and an osmotic polymer.

13. The osmotic pump of claim 1, wherein the osmotic composition is selected from the group consisting of osmotic tablets, powdered material, and flowable gel material.

14. The osmotic pump of claim 1, further comprising a filler distributed within or around the osmotic composition.

15. The osmotic pump of claim 1, wherein at least a portion of the rate controlling member is interference fit into the opening at the first end of the reservoir.

16. The osmotic pump of claim 1, wherein at least a portion of the rate controlling member is adhered into the opening at the first end of the reservoir.

17. The osmotic pump of claim 1, wherein a portion of the rate controlling member is initially filled by a plug formed of a material that degrades or erodes when exposed to the intended environment of operation.

* * * * *